US010632253B2

(12) United States Patent
Uchiyama et al.

(10) Patent No.: US 10,632,253 B2
(45) Date of Patent: Apr. 28, 2020

(54) LIQUID MEDICINE ADMINISTRATION APPARATUS AND LIQUID MEDICINE ADMINISTRATION UNIT

(71) Applicant: TERUMO KABUSHIKI KAISHA, Tokyo (JP)

(72) Inventors: Joji Uchiyama, Hadano (JP); Akira Kondo, Numazu (JP); Hideyuki Sato, Sendai (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 146 days.

(21) Appl. No.: 15/934,404

(22) Filed: Mar. 23, 2018

(65) Prior Publication Data

US 2018/0207358 A1    Jul. 26, 2018

Related U.S. Application Data

(63) Continuation of application No. PCT/JP2016/072852, filed on Aug. 3, 2016.

(30) Foreign Application Priority Data

Sep. 24, 2015 (JP) ................................. 2015-186755

(51) Int. Cl.
*A61M 5/168* (2006.01)
*A61M 5/142* (2006.01)
*A61M 5/145* (2006.01)

(52) U.S. Cl.
CPC ........ *A61M 5/16831* (2013.01); *A61M 5/142* (2013.01); *A61M 5/145* (2013.01);
(Continued)

(58) Field of Classification Search
CPC .......... A61M 2205/3389; A61M 39/10; A61M 5/14244; A61M 5/14566; A61M 5/16831;
(Continued)

(56) References Cited

U.S. PATENT DOCUMENTS

| 8,777,901 B2* | 7/2014 | Smith | ............... A61M 5/14216 604/151 |
| 2005/0020980 A1* | 1/2005 | Inoue | ................ A61M 5/14244 604/152 |

FOREIGN PATENT DOCUMENTS

| JP | 2007-511252 A | 5/2007 |
| JP | 2008-264140 A | 11/2008 |

(Continued)

OTHER PUBLICATIONS

Translation of the Written Opinion dated Nov. 8, 2016 in corresponding PCT application No. PCT/JP2016/072852.
(Continued)

*Primary Examiner* — Bhisma Mehta
*Assistant Examiner* — Rachel T. Smith
(74) *Attorney, Agent, or Firm* — Foley & Lardner LLP

(57) ABSTRACT

A liquid medicine administration apparatus includes: a drive section; an operation section configured to operate a pusher member that is slidably located in a liquid medicine container; a transmission mechanism configured to transmit a driving force of the drive section to the operation section; an occlusion detection mechanism located in the transmission mechanism and configured to detect occlusion of a passage of liquid medicine administered from the liquid medicine container; a rotation detector configured to detect rotation of the drive section; and a notification section configured to notify a user when the rotation detector detects stoppage of rotation of the drive section.

6 Claims, 17 Drawing Sheets

(52) U.S. Cl.
CPC ...... *A61M 5/1452* (2013.01); *A61M 5/14248* (2013.01); *A61M 5/168* (2013.01); *A61M 2005/16872* (2013.01); *A61M 2205/3306* (2013.01)

(58) Field of Classification Search
CPC ............ A61M 5/1452; A61M 5/14248; A61M 2205/3306; A61M 2005/16872; A61M 5/168; A61M 5/145; A61M 5/142
See application file for complete search history.

(56) References Cited

FOREIGN PATENT DOCUMENTS

| | | |
|---|---|---|
| JP | 2013-537844 A | 10/2013 |
| WO | WO-2015/146276 A1 | 10/2015 |

OTHER PUBLICATIONS

International Search Report with English language translation and Written Opinion dated Nov. 8, 2016 in International Application No. PCT/JP2016/072852.

\* cited by examiner

LIQUID MEDICINE ADMINISTRATION APPARATUS AND LIQUID MEDICINE ADMINISTRATION UNIT

CROSS-REFERENCE TO RELATED APPLICATIONS

The present application is a bypass continuation of PCT Application No. PCT/JP2016/072852, filed on Aug. 3, 2016, which claims priority to Japanese Application No. 2015-186755, filed on Sep. 24, 2015. The contents of these applications are hereby incorporated by reference in their entireties.

BACKGROUND

The present disclosure relates to a liquid medicine administration apparatus, and more particularly to a portable liquid medicine administration apparatus for sustainably administering liquid medicine, such as an insulin pump, and a liquid medicine administration unit including the liquid medicine administration apparatus.

In recent years, a treatment method of sustainably administering a liquid medicine to the body of a patient by subcutaneous injection, intravenous injection, or the like has been implemented. For example, treatment methods being applied to diabetes patients include a treatment of sustainably implementing infusion of a small amount of insulin into the body of the patient. This treatment method uses a portable liquid medicine administration apparatus (generally referred to as an insulin pump) that can be fixed to and carried with the patient's body or clothes to administer a liquid medicine (insulin) to the patient throughout the day.

One type of portable liquid medicine administration apparatus is a syringe pump type apparatus including a syringe storing a liquid medicine and a pusher driven inside the syringe. Such a liquid medicine administration apparatus includes an occlusion sensor to detect the occurrence of an occlusion of a liquid medicine passage. One example of an occlusion sensor has a configuration in which occlusion is detected using an encoder that controls rotation of a motor to drive a pusher, and a pressure sensor with a diaphragm provided on an outlet side of a liquid medicine (refer to JP 2013-537844 A, FIGS. 39 to 41, FIG. 93, and related descriptions).

SUMMARY

The technique described in JP 2013-537844 A, however, requires two sensor sections, an encoder for controlling rotation of the motor, and a pressure sensor provided on the outlet side of the liquid medicine in order to detect occlusion, leading to an increase in the number of components of the sensor section. In addition, it is difficult to perform highly accurate occlusion detection using the technique described in JP 2013-537844 A.

One object of certain embodiments is to provide a liquid medicine administration apparatus and a liquid medicine administration unit capable of performing occlusion detection with a simple configuration while reducing the number of components of the sensor section, and capable of detecting occlusion with high accuracy.

A liquid medicine administration apparatus according to one embodiment includes a drive section, an operation section, a transmission mechanism, an occlusion detection mechanism, a rotation detector, and a notification section. The operation section operates a pusher member slidably provided in a liquid medicine container to accommodate the liquid medicine. The transmission mechanism transmits driving force of the drive section to the operation section.

The occlusion detection mechanism is provided in the transmission mechanism and detects occlusion of the passage of the liquid medicine administered from the liquid medicine container. The rotation detector detects the rotation of the drive section. The notification section notifies the user when the rotation detector detects the stoppage of rotation of the drive section.

Moreover, the occlusion detection mechanism includes a drive side gear section, a pusher side gear section, and a locking mechanism. The drive side gear section meshes with a gear on the drive section side. The pusher side gear section rotates together with the drive side gear section and meshes with a gear on the operation section side. The locking mechanism stops rotation of the drive side gear section when rotational resistance applied to the pusher side gear section exceeds a predetermined force.

Moreover, the liquid medicine administration unit according to one embodiment includes: a liquid medicine administration apparatus including a liquid medicine container to accommodate a liquid medicine; a cradle apparatus to which the liquid medicine administration apparatus is detachably attached; and a connection port to be attached to the cradle apparatus and including a cannula to be punctured in a living body and to which a liquid medicine is supplied from a liquid medicine administration apparatus.

According to certain embodiments of the liquid medicine administration apparatus and the liquid medicine administration unit described herein, it is possible to reduce the number of components of the sensor section and detect occlusion using a simple configuration with high accuracy.

DETAILED DESCRIPTION

Figure 1:
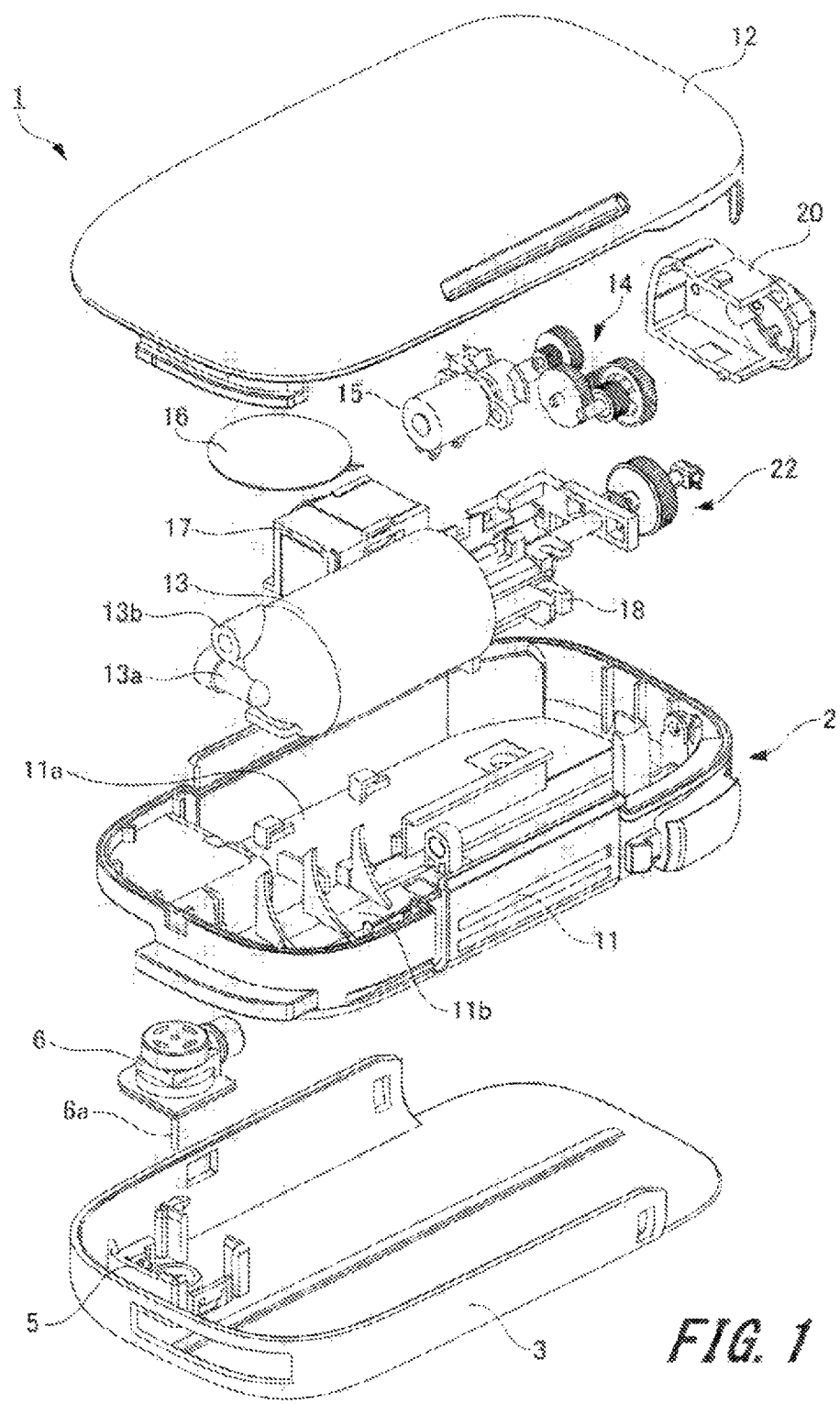
FIG. 1 is an exploded perspective view illustrating a liquid medicine administration unit according to a first exemplary embodiment.

Hereinafter, embodiments of a liquid medicine administration unit and a liquid medicine administration apparatus will be described with reference to FIGS. 1 to 17. In the drawings, common members are denoted by the same reference numerals. The present invention is not limited to the following embodiments.

1. First Exemplary Embodiment 1-1. Exemplary Configuration of Liquid Medicine Administration Unit First, an exemplary configuration of a liquid medicine administration unit according to a first exemplary embodiment (hereinafter referred to as "the example" or "the exemplary case") will be described with reference to FIG. 1.

FIG. 1 is an exploded perspective view illustrating a liquid medicine administration unit.

The apparatus illustrated in FIG. 1 is universally applied to a portable liquid medicine administration unit for sustainably administering a liquid medicine into the patient, such as a patch type insulin pump, a tubular type insulin pump, and other portable type liquid medicine administration apparatus. As illustrated in FIG. 1, the liquid medicine administration unit 1 includes a liquid medicine administration apparatus 2, a cradle apparatus 3 to which the liquid medicine administration apparatus 2 is detachably attached, and a connection port 6 to be attached to the cradle apparatus 3.

The cradle apparatus 3 includes an attachment section 5 to which the connection port 6 is attached. The connection port 6 includes a cannula 6a. The cradle apparatus 3 is adhered to the patient's skin to allow the connection port 6 to be attached to the attachment section 5 using a puncturing mechanism (not illustrated). When the connection port 6 is attached to the attachment section 5 of the cradle apparatus 3, the cannula 6a protrudes from the side of the cradle apparatus 3 opposite to the side on which the liquid medicine administration apparatus 2 is attached, so as to allow the cannula 6a to be punctured and left in a living body. When the liquid medicine administration apparatus 2 is attached in a state in which the connection port 6 is attached to the cradle apparatus 3, the connection port 6 is housed in a back surface housing of a casing 11 of the liquid medicine administration apparatus 2 described below. The connection port 6 is connected to a liquid delivery pipe 19 of the liquid medicine administration apparatus 2, as shown in FIG. 2.

[Liquid medicine Administration Apparatus]

Next, the liquid medicine administration apparatus 2 will be described with reference to FIGS. 1, 2 and 3.

Figure 2:
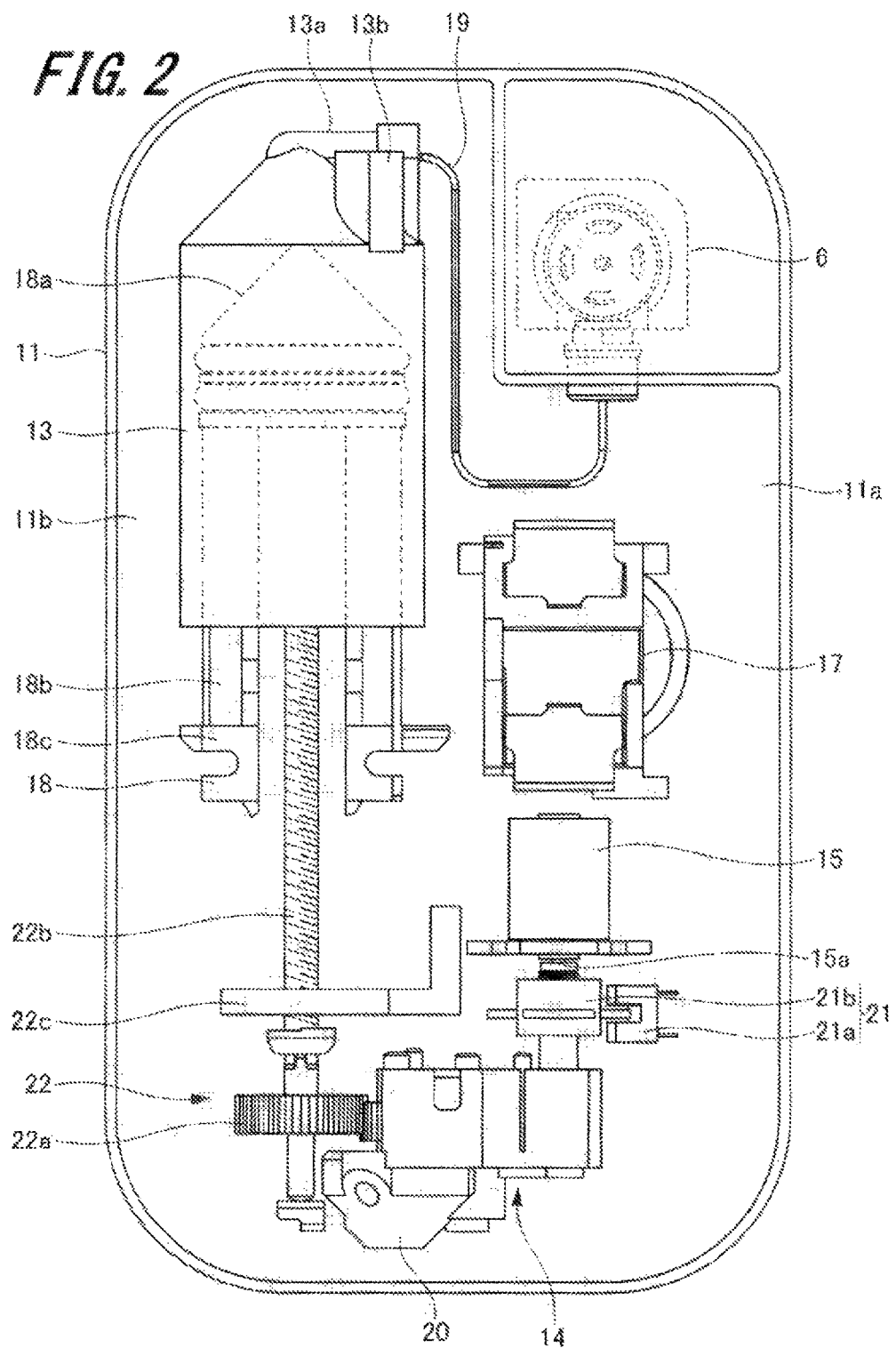
FIG. 2 is a plan view illustrating a liquid medicine administration apparatus according to a first exemplary embodiment.
Figure 3:
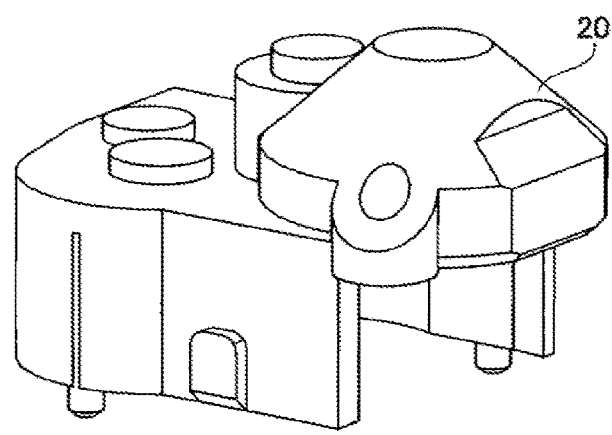
FIG. 3 is a perspective view illustrating a transmission mechanism of the liquid medicine administration apparatus according to the first exemplary embodiment.
Figure 3:
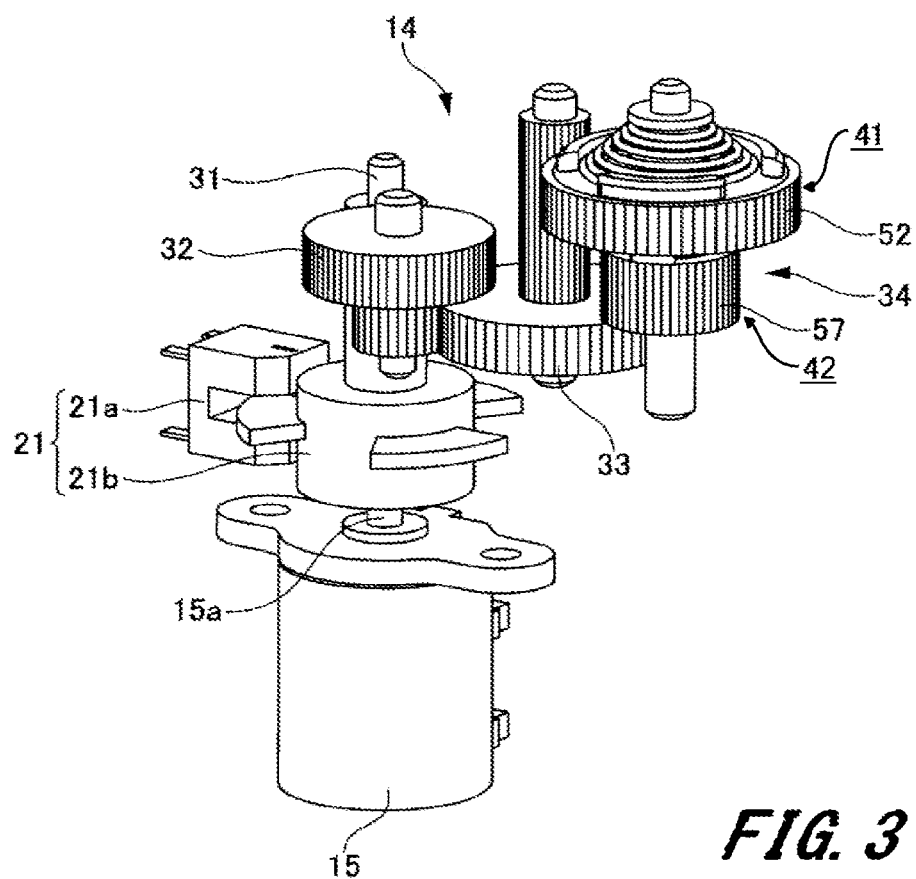

FIG. 2 is a plan view illustrating the liquid medicine administration apparatus 2, and FIG. 3 is a perspective view illustrating a transmission mechanism.

As illustrated in FIGS. 1 and 2, the liquid medicine administration apparatus 2 includes a casing 11, a lid member 12, a liquid medicine storage 13, a transmission mechanism 14, a drive section 15, a notification section 16, a battery housing 17, a pusher member 18, a rotation detector 21, and an operation section 22 to operate the pusher member 18. The liquid medicine administration apparatus 2 further includes the liquid delivery pipe 19 connected to the liquid medicine storage 13 and a control substrate (not illustrated).

The casing 11 has a hollow substantially rectangular parallelepiped shape with one surface open. The casing 11 includes a first housing 11a and a second housing 11b. The first housing 11a houses the drive section 15, the battery housing 17, the rotation detector 21, and a portion of the transmission mechanism 14. The second housing 11b houses the liquid medicine storage 13, the pusher member 18, the operation section 22, and a portion of the transmission mechanism 14.

The lid member 12 has a substantially flat plate shape. The lid member 12 covers the first housing 11a and the second housing 11b included in the casing 11 and closes the opening of the casing 11. The transmission mechanism 14, the drive section 15, the notification section 16, and the rotation detector 21 are fixed to the lid member 12.

The liquid medicine storage 13 has a cylindrical shape having one axial end closed and the other axial end open. A liquid medicine is stored in a cylindrical hole of the liquid medicine storage 13. One axial end portion of the liquid medicine storage 13 includes a liquid delivery port 13a and a filling port 13b. The liquid delivery port 13a is connected to the liquid delivery pipe 19, and the liquid medicine stored in the liquid medicine storage 13 is discharged through the liquid delivery port 13a.

A filling apparatus (not illustrated) is connected to the filling port 13b. The liquid medicine is filled into the cylindrical hole of the liquid medicine storage 13 via the filling port 13b. Moreover, the pusher member 18 is slidably inserted in the cylindrical hole of the liquid medicine storage 13.

The pusher member 18 includes a gasket 18a and a shaft member 18b. The gasket 18a is slidably disposed within the cylindrical hole of the liquid medicine storage 13. The gasket 18a moves in close contact with an inner peripheral surface of the cylindrical hole of the liquid medicine storage 13 in a liquid-tight manner. The shape of a distal end portion of the gasket 18a corresponds to the shape of one axial end side of the cylindrical hole of the liquid medicine storage 13. With this configuration, when the gasket 18a moves to one axial end side of the liquid medicine storage 13, the liquid medicine filled in the liquid medicine storage 13 can be discharged from the liquid delivery port 13a without waste.

The shaft member 18b is provided on the opposite side of the distal end portion of the gasket 18a. The shaft member 18b extends outward from an opening formed at the other axial end of the liquid medicine storage 13. The end portion of the shaft member 18b on the side opposite to the gasket 18a includes a coupling portion 18c to engage with a coupling nut 22c of the operation section 22 described below. When the coupling portion 18c is coupled with the coupling nut 22c to drive the operation section 22, the pusher member 18 moves along the axial direction of the liquid medicine storage 13.

The operation section 22 includes an operation gear 22a, a feed screw shaft 22b, and a coupling nut 22c. The operation gear 22a meshes with a pusher side gear 57 of the transmission mechanism 14 described below. The feed screw shaft 22b is connected to the rotation shaft of the operation gear 22a. The feed screw shaft 22b is disposed in parallel with the shaft member 18b in a state rotatably supported by a bearing provided in the casing 11.

A coupling nut 22c is screwed to the feed screw shaft 22b. When the coupling nut 22c is housed in the second housing 11b of the casing 11, the circumferential rotation of the feed screw shaft 22b is restricted. Accordingly, when the operation gear 22a rotates to rotate the feed screw shaft 22b, the coupling nut 22c moves along the axial direction of the feed screw shaft 22b. When the coupling portion 18c of the pusher member 18 is engaged with the coupling nut 22c, the pusher member 18 moves together with the coupling nut 22c along the axial direction of the feed screw shaft 22b. Driving force of the drive section 15 is transmitted to the operation section 22 via the transmission mechanism 14.

The drive section 15 is driven by a battery housed in the battery housing 17. As the drive section 15, for example, a stepping motor is applied. In a state in which the opening of the casing 11 is closed by the lid member 12, the drive section 15 is connected to electrodes of the battery housing 17 housed in the casing 11 to be powered. The drive shaft 15a of the drive section 15 includes a rotation detector 21 to detect the rotation of the drive shaft 15a.

The rotation detector 21 is a rotary encoder including a detection sensor 21a and a slit disk 21b. The slit disk 21b is fixed to the drive shaft 15a of the drive section 15. The slit disk 21b rotates in synchronization with the rotation of the drive shaft 15a. Slits are formed at equal intervals on the periphery of the slit disk 21b.

The detection sensor 21a is disposed in the first housing 11a of the casing 11. The detection sensor 21a is an optical sensor having a light emitting portion to emit light and a light receiving portion to receive the light emitted from the light emitting portion. The detection sensor 21a detects the light transmitted through the slit of the slit disk 21b to detect rotation of the drive section 15.

The drive shaft 15a of the drive section 15 includes a first gear 31 of the transmission mechanism 14. As illustrated in FIG. 3, the transmission mechanism 14 transmits the driving force (rotation) of the drive section 15 to the operation section 22. The transmission mechanism 14 includes the first gear 31, a second gear section 32, a third gear section 33, and an occlusion detection mechanism 34. The transmission mechanism 14 is accommodated in a gear case 20.

The first gear 31 is provided on the drive shaft 15a of the drive section 15. The first gear 31 rotates in synchronization with the drive shaft 15a of the drive section 15. The first gear 31 meshes with a gear of the second gear section 32 for deceleration. A gear besides the gear meshing with the first gear 31 in the second gear section 32 meshes with a gear of the third gear section 33. The gear of the third gear section 33, besides the gear meshing with the gear of the second gear section 32, meshes with a drive side gear 52 of the occlusion detection mechanism 34. Moreover, the pusher side gear 57 of the occlusion detection mechanism 34 meshes with the operation gear 22a of the operation section 22.

As illustrated in FIG. 3, the drive of the drive section 15 rotates the first gear 31, the second gear section 32, the third gear section 33, and a drive side gear section 41 and a pusher side gear section 42 of the occlusion detection mechanism 34, to be described below. This operation transmits the driving force of the drive section 15 to the operation gear 22a via the transmission mechanism 14.

[Gear Case]

Next, the gear case 20 will be described with reference to FIG. 4.

Figure 4:
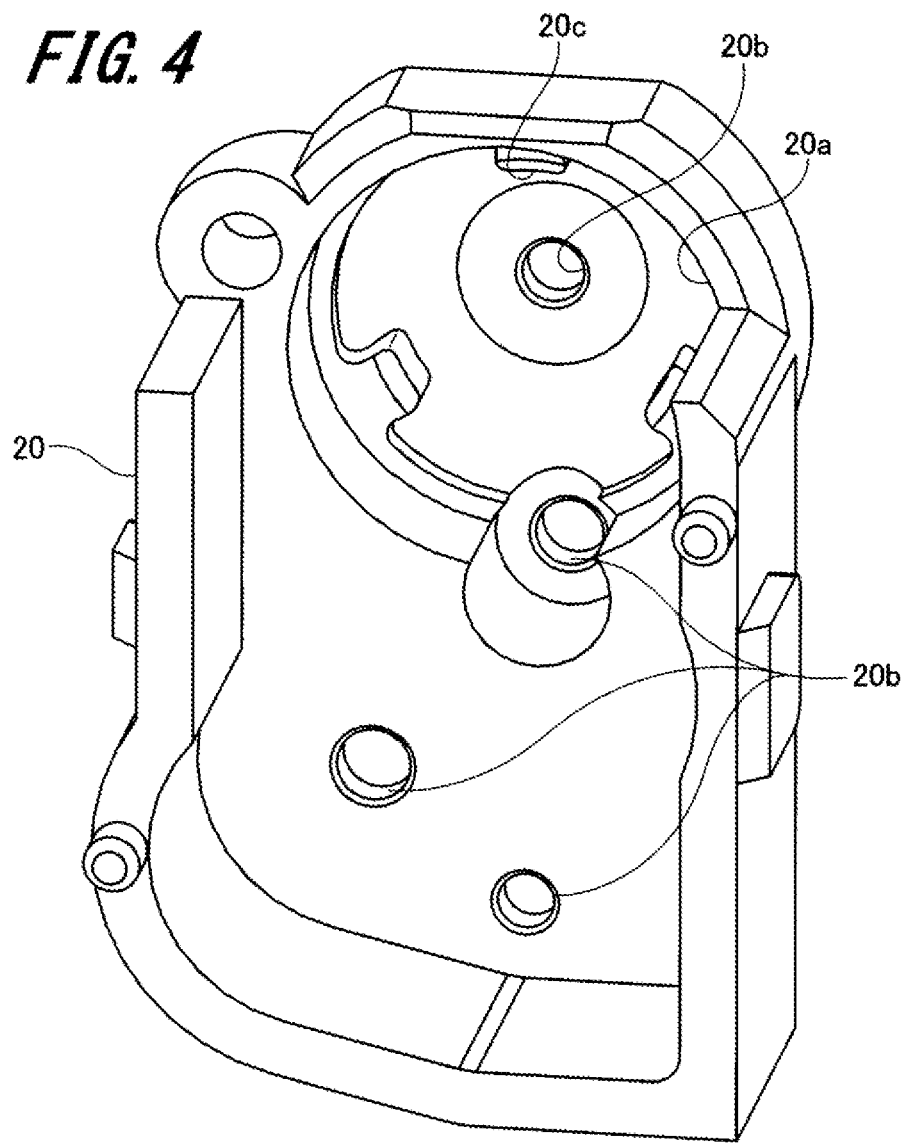
FIG. 4 is a perspective view illustrating a gear case of the liquid medicine administration apparatus according to the first exemplary embodiment.

FIG. 4 is a perspective view illustrating the gear case 20.

As illustrated in FIG. 4, the gear case 20 has a hollow container shape with one surface open. The gear case 20 includes an insertion section 20a into which a portion of the occlusion detection mechanism 34, described below, is inserted. The insertion section 20a is formed by allowing a portion of the gear case 20 to bulge in a substantially conical shape in a direction opposite to the opening.

A plurality of protrusions 20c are formed on an outer edge portion of the insertion section 20a on the opening side. The plurality of protrusions 20c are disposed at equal intervals along the circumferential direction of the outer edge portion of the insertion section 20a. When the occlusion detection mechanism 34 to be described below detects occlusion of the liquid medicine passage, the fixing protrusions 53 provided in the occlusion detection mechanism 34 (refer to FIG. 10) abuts the plurality of protrusions 20c.

The gear case 20 includes the first gear 31, the second gear section 32, the third gear section 33, and a plurality of bearing portions 20b to rotatably support the occlusion detection mechanism 34 to be described below.

[Occlusion Detection Mechanism]

Next, the occlusion detection mechanism 34 will be described with reference to FIGS. 5 to 8.

Figure 5:
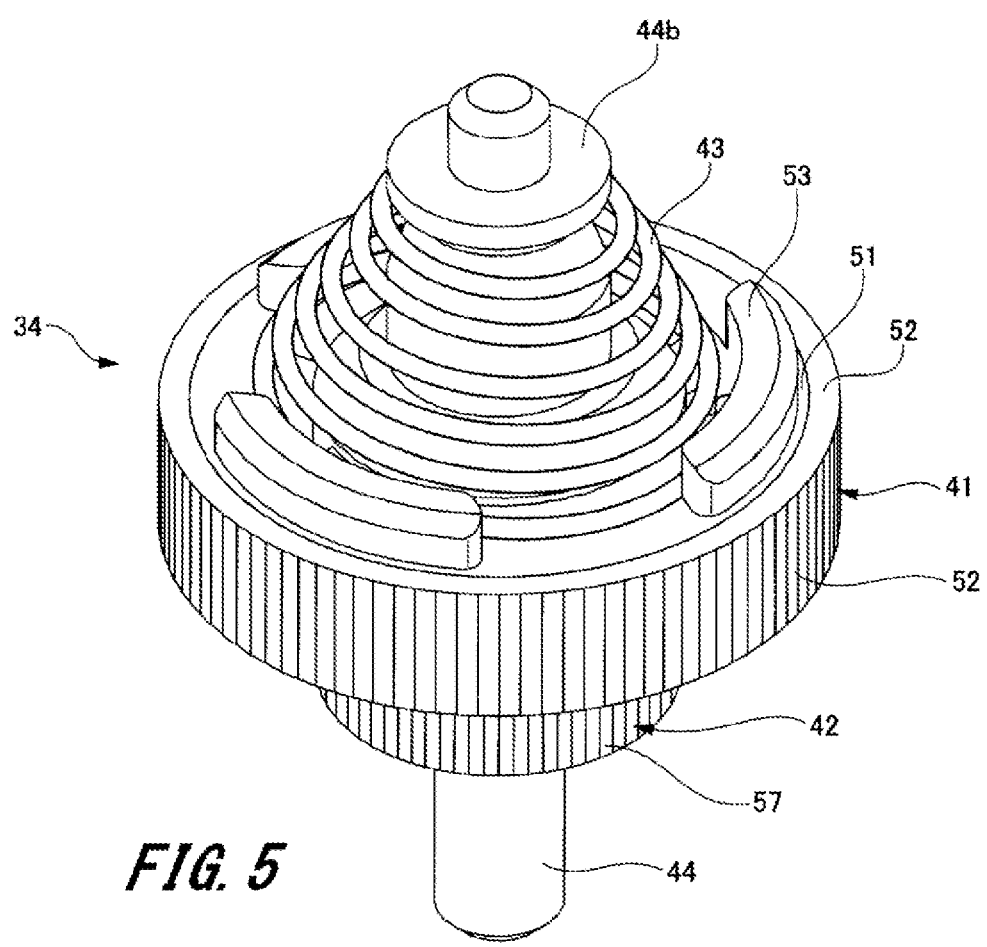
FIG. 5 is a perspective view illustrating an occlusion detection mechanism of the liquid medicine administration apparatus according to the first exemplary embodiment.
Figure 6:
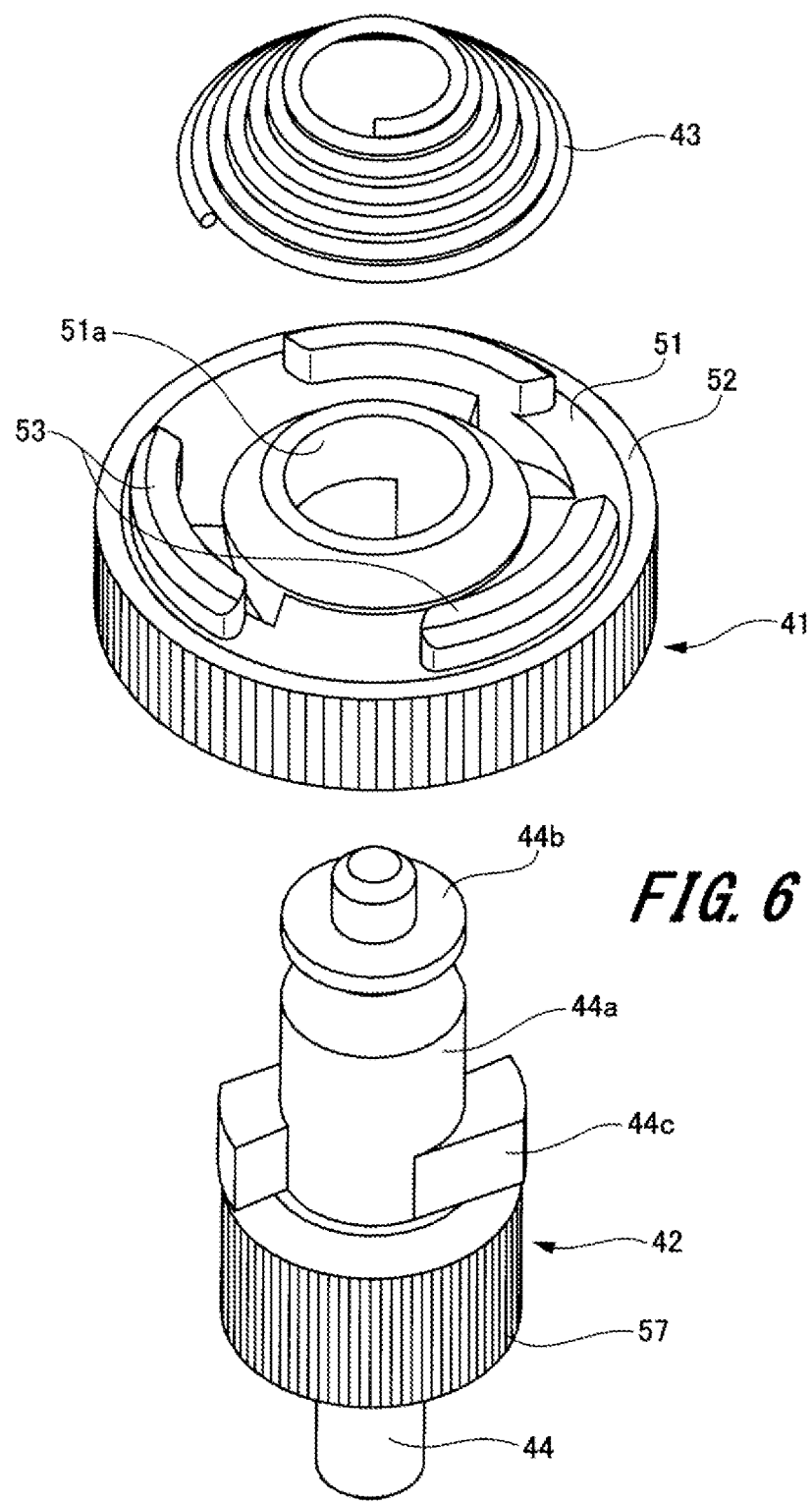
FIG. 6 is an exploded perspective view illustrating the occlusion detection mechanism of the liquid medicine administration apparatus according to the first exemplary embodiment.
Figure 7:
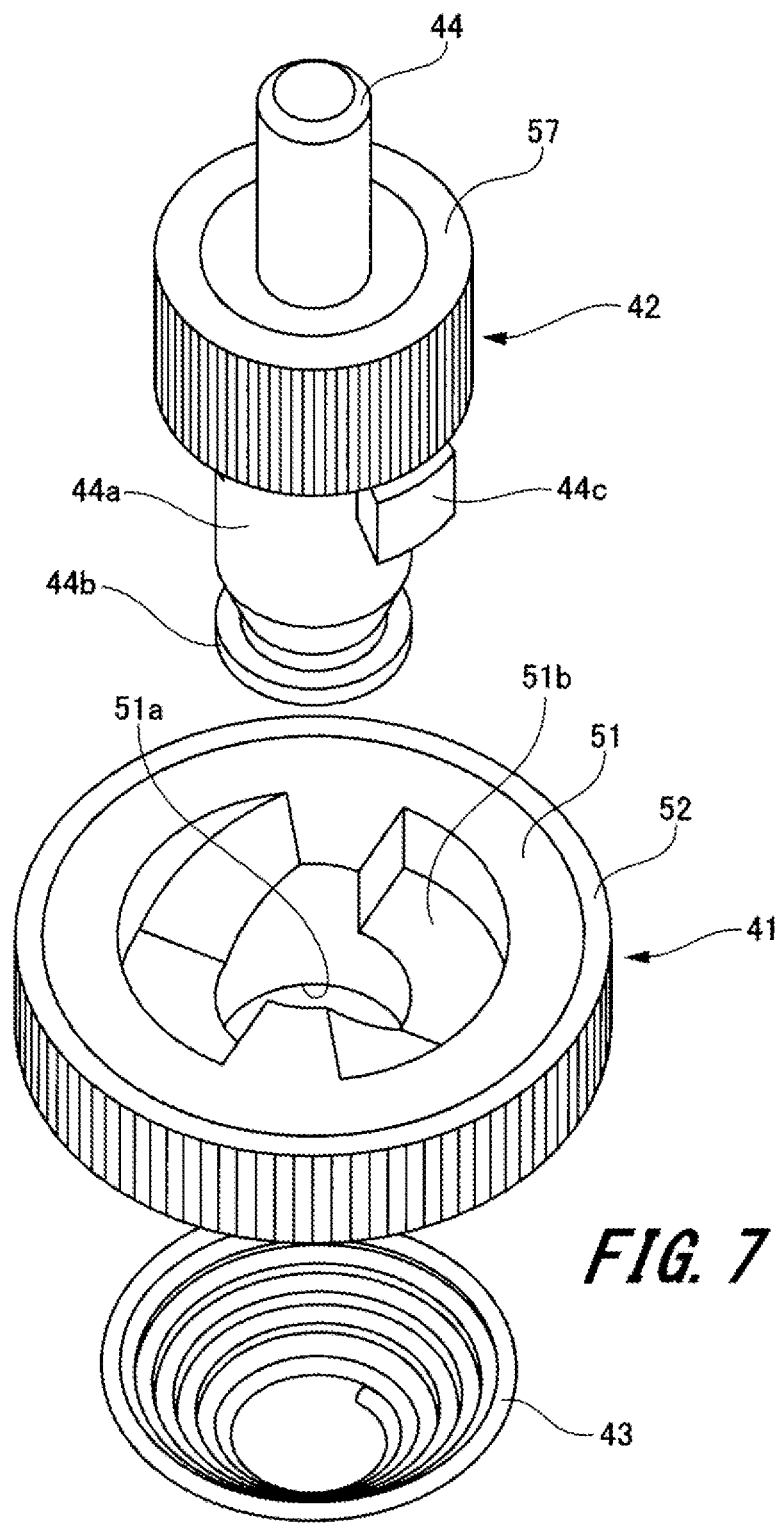
FIG. 7 is an exploded perspective view illustrating the occlusion detection mechanism of the liquid medicine administration apparatus according to the first exemplary embodiment.
Figure 8:
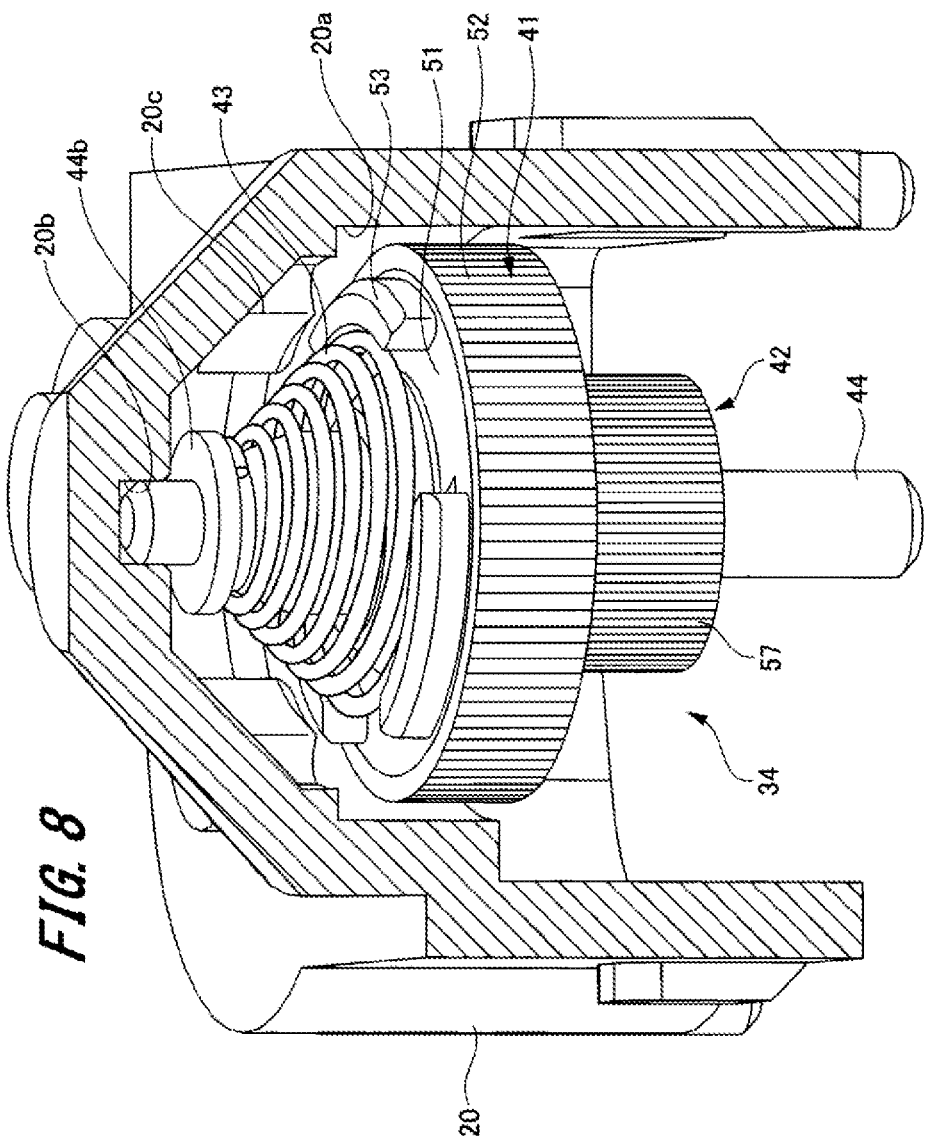
FIG. 8 is an explanatory view illustrating a state in which the occlusion detection mechanism of the liquid medicine administration apparatus according to the first exemplary embodiment is accommodated in a gear case.

FIG. 5 is a perspective view illustrating the occlusion detection mechanism 34, and FIGS. 6 and 7 are exploded perspective views illustrating the occlusion detection mechanism 34. FIG. 8 is an explanatory view illustrating a state in which the occlusion detection mechanism 34 is accommodated in the gear case 20.

As illustrated in FIGS. 5 to 8, the occlusion detection mechanism 34 includes the drive side gear section 41, the pusher side gear section 42, a biasing member 43, and a rotation shaft 44.

The drive side gear section 41 includes a main body 51, the drive side gear 52, and a plurality of fixing protrusions 53. The main body 51 has a columnar shape. A through hole 51a is formed at a center of the main body 51 in the radial direction. The through hole 51a penetrates the main body 51 from one axial end to the other axial end. The rotation shaft 44 penetrates through the through hole 51a.

A cam groove 51b is formed on one surface of the main body 51 on one axial end side. The cam groove 51b is formed so as to surround the periphery of the through hole 51a. In addition, the cam groove 51b is formed by recessing one surface on the one end side of the main body 51 toward the other end side. A cam pin 44c provided on the rotation shaft 44 is inserted into the cam groove 51b.

The plurality of fixing protrusions 53 are formed on one surface on the other axial end side of the main body 51. The plurality of fixing protrusions 53 are disposed at equal intervals in the circumferential direction of the main body 51 at the outer edge portion of the main body 51. The plurality of fixing protrusions 53 axially protrudes from one surface on the other axial end side of the main body 51. The plurality of fixing protrusions 53 provided on the drive side gear section 41 and the protrusions 20*c* provided on the gear case 20 constitute a fixing mechanism.

As illustrated in FIG. 8, when the drive side gear section 41 is accommodated in the gear case 20, the main body 51 faces the opening of the insertion section 20*a* in a state before detecting an occlusion state.

The drive side gear 52 is formed on a side peripheral portion of the main body 51. The drive side gear 52 meshes with the gear of the third gear section 33 (refer to FIG. 3).

The pusher side gear section 42 is formed integrally with the rotation shaft 44. The pusher side gear section 42 includes the pusher side gear 57 meshed with the operation gear 22*a* of the operation section 22.

The rotation shaft 44 includes a shaft section 44*a*, a spring receiving piece 44*b*, and the cam pin 44*c*. The pusher side gear section 42 is provided at one axial end portion of the shaft section 44*a*. The spring receiving piece 44*b* is formed at the other axial end of the shaft section 44*a*. The spring receiving piece 44*b* has a disk shape. The biasing member 43 described below abuts the spring receiving piece 44*b*.

The cam pin 44*c* is formed in the vicinity of the pusher side gear section 42 on the shaft section 44*a* and is disposed on the other axial end side with respect to the pusher side gear section 42. The cam pin 44*c* is inserted into the cam groove 51*b* provided on the main body 51 of the drive side gear section 41.

The shaft section 44*a* penetrates through the through hole 51*a* of the drive side gear section 41. The drive side gear section 41 is disposed between the pusher side gear section 42 and the spring receiving piece 44*b*, provided on the shaft section 44*a*. As illustrated in FIG. 8, the other axial end of the shaft section 44*a* is inserted into the insertion section 20*a* of the gear case 20 and is rotatably supported by the bearing portion 20*b*.

The biasing member 43 as an exemplary temporary retainer is constituted with a compression coil spring formed in a truncated cone shape. The biasing member 43 is interposed between the drive side gear section 41 and the spring receiving piece 44*b*, attached to the rotation shaft 44. One end portion of the biasing member 43 abuts one surface on the other axial end side of the main body 51 of the drive side gear section 41, and the other end portion on the opposite side of the biasing member 43 abuts the spring receiving piece 44*b*. The biasing member 43 biases the drive side gear section 41 toward one axial side of the shaft section 44*a*, that is, toward the pusher side gear section 42 with predetermined force.

While the above description is an exemplary case where the biasing member 43 formed of a compression coil spring is applied as an exemplary temporary retainer, the present invention is not limited to this exemplary case. The temporary retainer may be any member as long as it can bias the drive side gear section 41 in a direction of separating the fixing protrusion 53 away from the protrusion 20*c* of the gear case 20, that is, as long as it can bias the drive side gear section 41 to the one axial side of the shaft section 44*a*, for example a member such as a leaf spring, and other various elastic members is applicable.

[Notification Section]

Now, the notification section 16 will be described.

The notification section 16 is connected to the detection sensor 21*a* of the rotation detector 21. When the rotation detector 21 detects stoppage of rotation of the drive section 15, the notification section 16 notifies the user of the stoppage by a sound, light emission, vibration, for example. Alternatively, the notification section 16 can notify the user by wirelessly activating a controller (not illustrated) held by the user.

1-2. Occlusion Detection Operation

Next, occlusion detection operation of the occlusion detection mechanism 34 having the above-described configuration will be described with reference to FIGS. 9 to 10.

Figure 9:
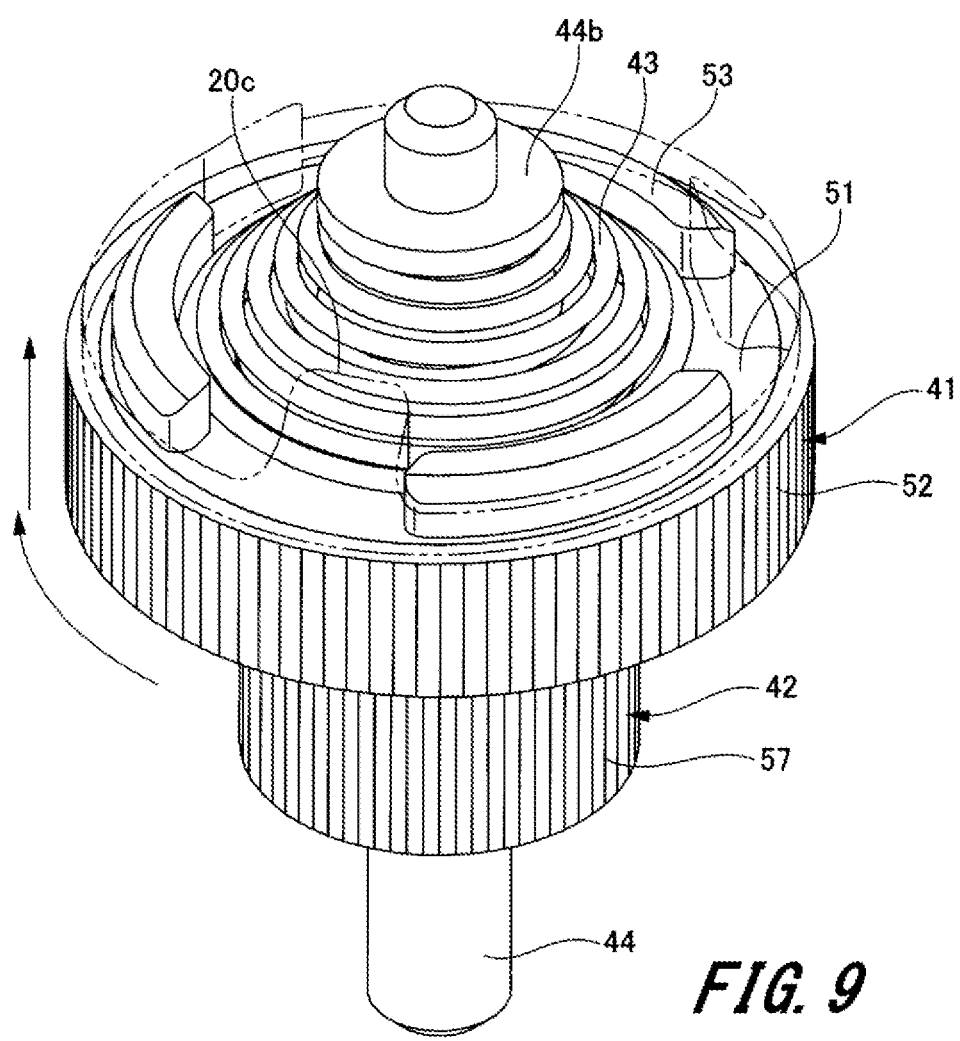
FIG. 9 is an explanatory view illustrating occlusion detection operation of the occlusion detection mechanism of the liquid medicine administration apparatus according to the first exemplary embodiment.
Figure 10:
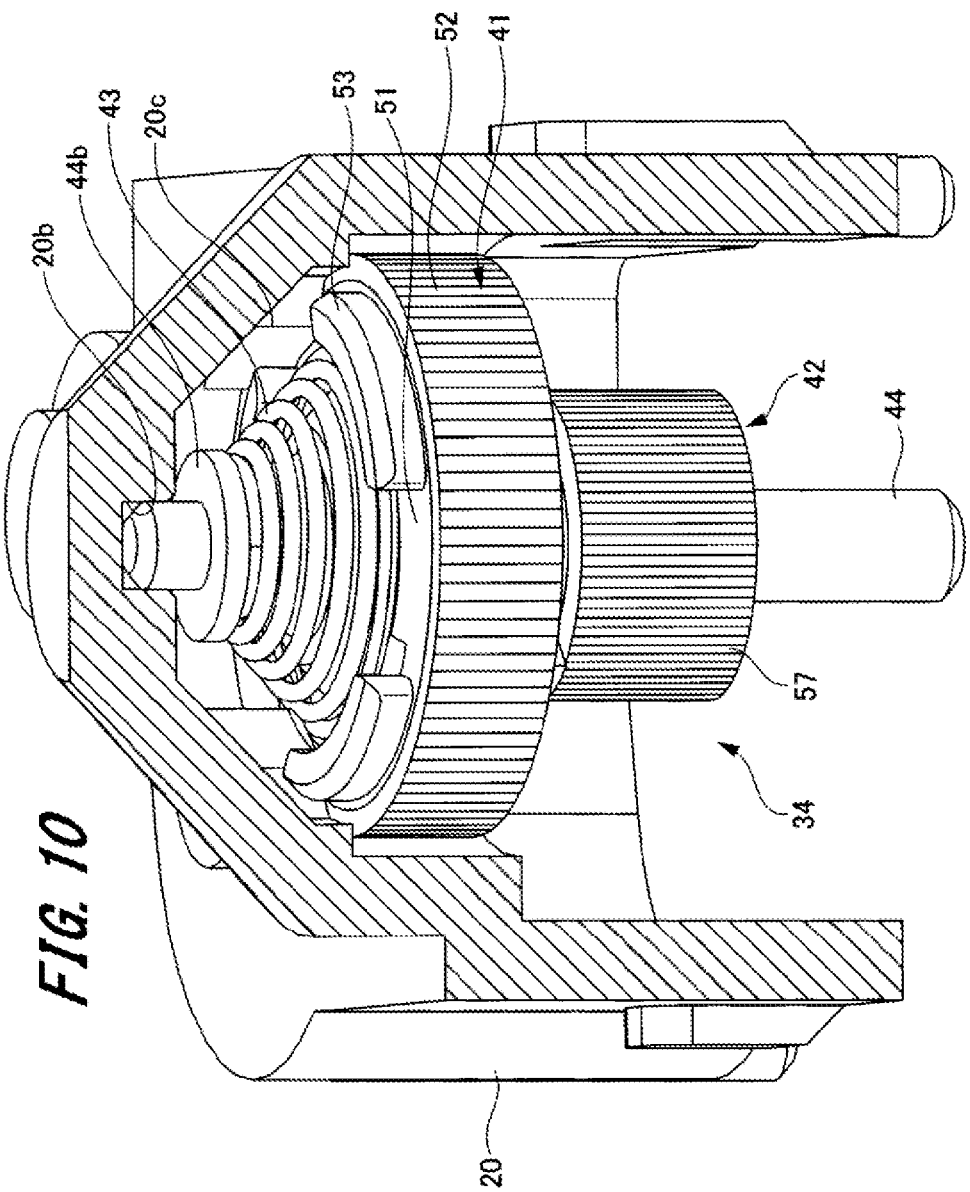
FIG. 10 is an explanatory view illustrating occlusion detection operation of the occlusion detection mechanism of the liquid medicine administration apparatus according to the first exemplary embodiment.

FIGS. 9 and 10 are explanatory view illustrating occlusion detection operation of the occlusion detection mechanism 34.

First, in a state in which the liquid medicine passage such as the cannula 6*a* is not occluded, the drive side gear section 41 is biased toward the pusher side gear section 42 by the biasing member 43 as illustrated in FIGS. 5 and 8. Therefore, the main body 51 of the drive side gear section 41 faces the insertion section 20*a* of the gear case 20, without allowing the fixing protrusion 53 to abut the protrusion 20*c*. Moreover, because the cam pin 44*c* is inserted in the cam groove 51*b*, the drive side gear section 41 rotates together with the rotation shaft 44 and the pusher side gear section 42. This rotates the operation gear 22*a* meshing with the pusher side gear 57 of the pusher side gear section 42 to further rotate the feed screw shaft 22*b* fixed to the operation gear 22*a*.

In contrast, when the passage of the liquid medicine pushed out by the pusher member 18 is occluded due to a certain factor, rotational resistance (torque) applied to the operation gear 22*a* via the feed screw shaft 22*b* increases. This increases the torque applied to the pusher side gear 57 of the pusher side gear section 42 via the operation gear 22*a*, delaying the rotation of the pusher side gear section 42.

Here, the driving force from the drive section 15 is transmitted to the drive side gear section 41. This generates, as illustrated in FIG. 9, a phase difference between the rotation of the drive side gear section 41, and the rotation of the rotation shaft 44 and the pusher side gear section 42, so as to cause the cam pin 44*c* to slide in the cam groove 51*b*. This causes the drive side gear section 41 to move along the axial direction of the shaft section 44*a*, against biasing force of the biasing member 43, toward the other axial end side, that is, toward the insertion section 20*a* of the gear case 20.

As illustrated in FIG. 10, the locking mechanism comprises a protrusion 20*c* and a fixing protrusion 53. The fixing protrusion 53 of the drive side gear section 41 abuts the protrusion 20*c* provided on the gear case 20. This locks the rotation of the drive side gear section 41. When the rotation of the drive side gear section 41 is locked, the rotation of the third gear section 33 meshing with the drive side gear 52 of the drive side gear section 41 is also locked. This also locks the rotation of the second gear section 32 and the first gear 31 to stop the rotation of the drive shaft 15*a* of the drive section 15, so as to induce step-out of the drive section 15.

The stoppage of the rotation of the drive section 15 can be detected by the rotation detector 21. As a result, the notification section 16 is activated to notify the user of the occluded state. According to the above-described occlusion detection mechanism 34, because the torque actually applied to the transmission mechanism 14 is detected, it is possible to enhance occlusion detection accuracy.

Moreover, according to the occlusion detection mechanism 34 in the exemplary case, it is possible to detect occlusion using the rotation detector 21 that detects the rotation of the drive section 15. As a result, it is possible to detect occlusion with a simple configuration without another detector to detect occlusion.

While the liquid medicine administration apparatus 2 in the exemplary case is an example in which the protrusion 20c that abuts the fixing protrusion 53 of the drive side gear section 41 is provided in the gear case 20, the invention is not limited to this example. For example, the gear case 20 may be omitted and a protrusion to abut the fixing protrusion 53 may be provided on the casing 11.

Moreover, when the occlusion of the liquid medicine passage is overcome and the drive of the drive section 15 is restored, the drive side gear section 41 is biased to one axial side of the rotation shaft 44 by the biasing force of the biasing member 43. This automatically restores the lock state illustrated in FIG. 9 and FIG. 10 to the initial state illustrated in FIGS. 5 and 8. This makes it possible to use the liquid medicine administration apparatus 2 again.

Furthermore, in the occlusion detection mechanism 34 in the exemplary case, the biasing force of the biasing member 43 can be adjusted to change the occlusion detection accuracy according to the purpose.

While the liquid medicine administration apparatus 2 described above is an example in which the occlusion detection mechanism 34 is provided in the final stage gear of the transmission mechanism 14, the present invention is not limited to this example. The occlusion detection mechanism 34 described above may be applied to any of the plurality of gears constituting the transmission mechanism 14 to transmit the driving force of the drive section 15 to the operation section 22.

2. Second Exemplary Embodiment

Next, a liquid medicine administration unit and a liquid medicine administration apparatus according to a second exemplary embodiment will be described with reference to FIGS. 11 to 17.

Figure 11:
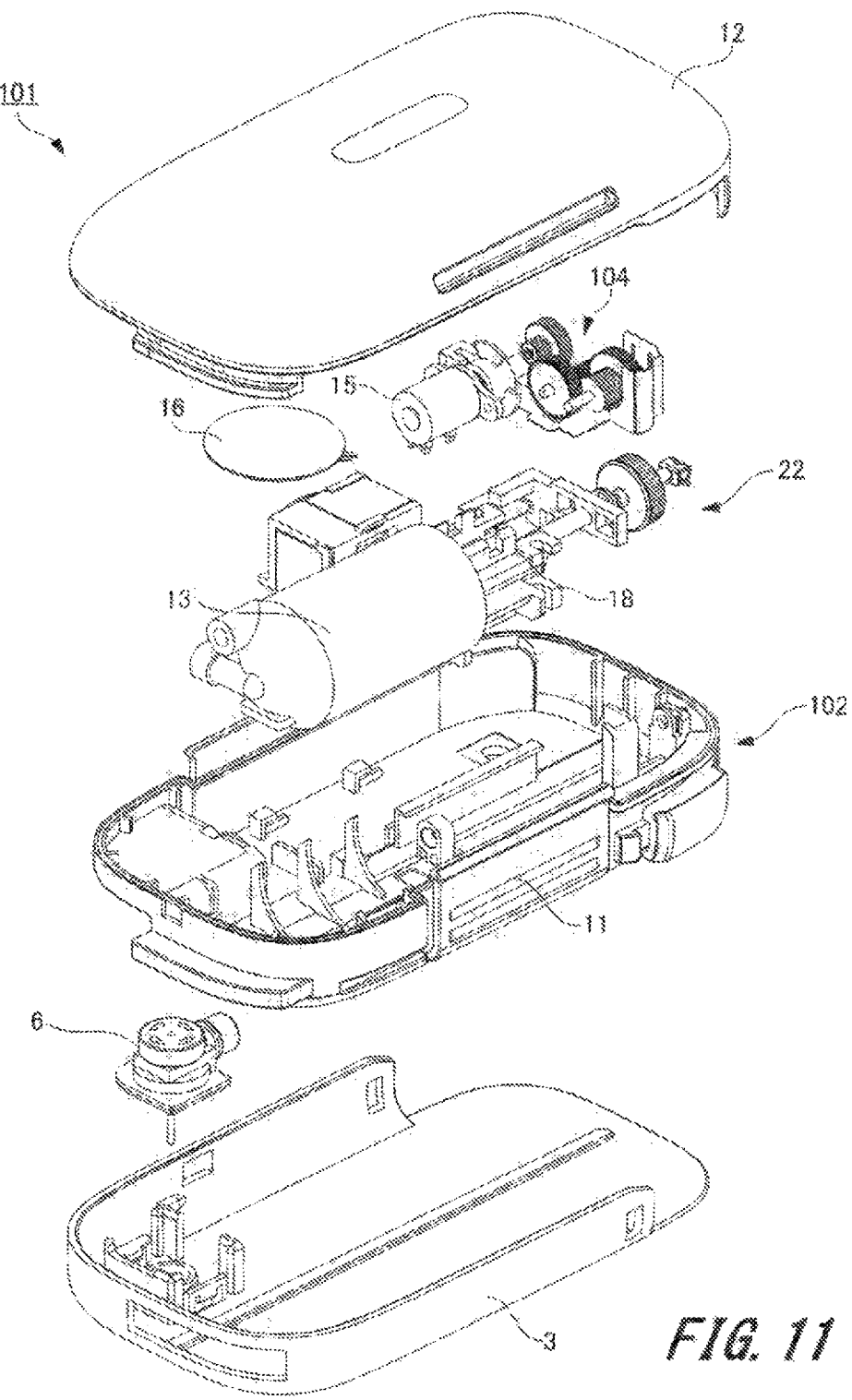
FIG. 11 is an exploded perspective view illustrating a liquid medicine administration unit according to a second exemplary embodiment.
Figure 12:
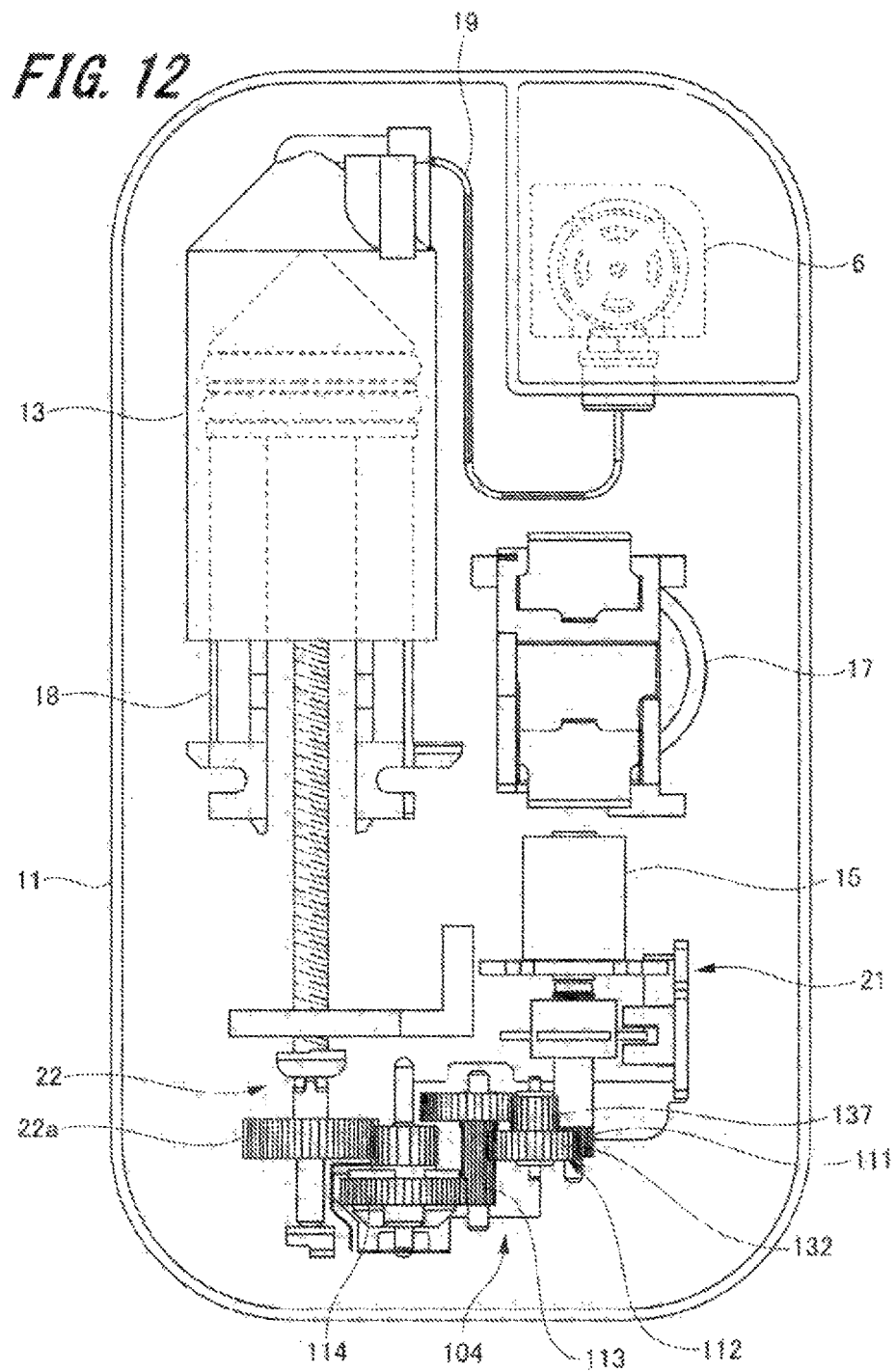
FIG. 12 is a plan view illustrating a liquid medicine administration apparatus according to the second exemplary embodiment.

FIG. 11 is an exploded perspective view illustrating a liquid medicine administration unit, and FIG. 12 is a plan view illustrating a liquid medicine administration apparatus.

The liquid medicine administration unit according to the second exemplary embodiment is different from the liquid medicine administration unit 1 according to the first exemplary embodiment in the configuration of the occlusion detection mechanism. Accordingly, the occlusion detection mechanism will be mainly described herein and the same reference numerals are given to portions common to the liquid medicine administration unit 1 according to the first exemplary embodiment, and redundant explanations will be omitted.

As illustrated in FIGS. 11 and 12, the liquid medicine administration unit 101 includes a liquid medicine administration apparatus 102, the cradle apparatus 3, and the connection port 6. The liquid medicine administration apparatus 102 includes the casing 11, the lid member 12, the liquid medicine storage 13, the drive section 15, the notification section 16, the battery housing 17, the pusher member 18, the rotation detector 21, and the operation section 22. The liquid medicine administration apparatus 102 further includes a transmission mechanism 104.

The transmission mechanism 104 includes a first gear 111, an occlusion detection mechanism 112 having a drive side gear 132 meshed with the first gear 111, and a third gear section 113 meshing with a pusher side gear 137 of the occlusion detection mechanism 112, and a fourth gear section 114 meshing with the third gear section 113. The fourth gear section 114 meshes with the operation gear 22a of the operation section 22.

Next, the occlusion detection mechanism 112 will be described with reference to FIGS. 13 to 16.

Figure 13:
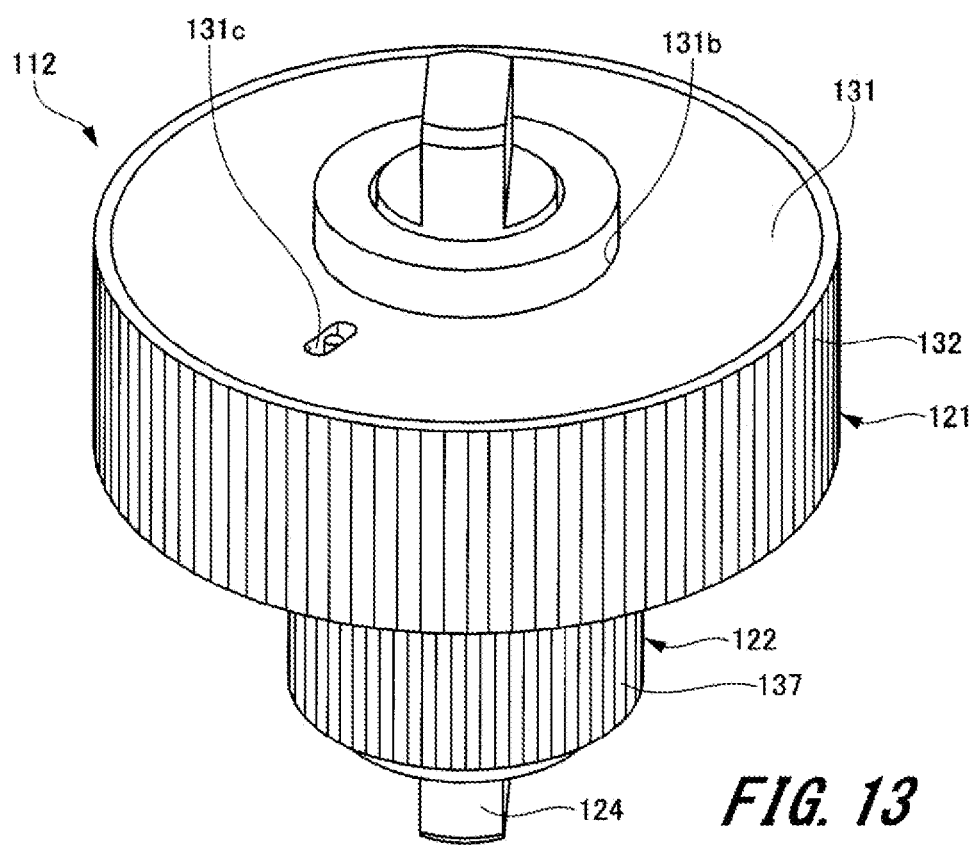
FIG. 13 is a perspective view illustrating an occlusion detection mechanism of the liquid medicine administration apparatus according to the second exemplary embodiment.
Figure 14:
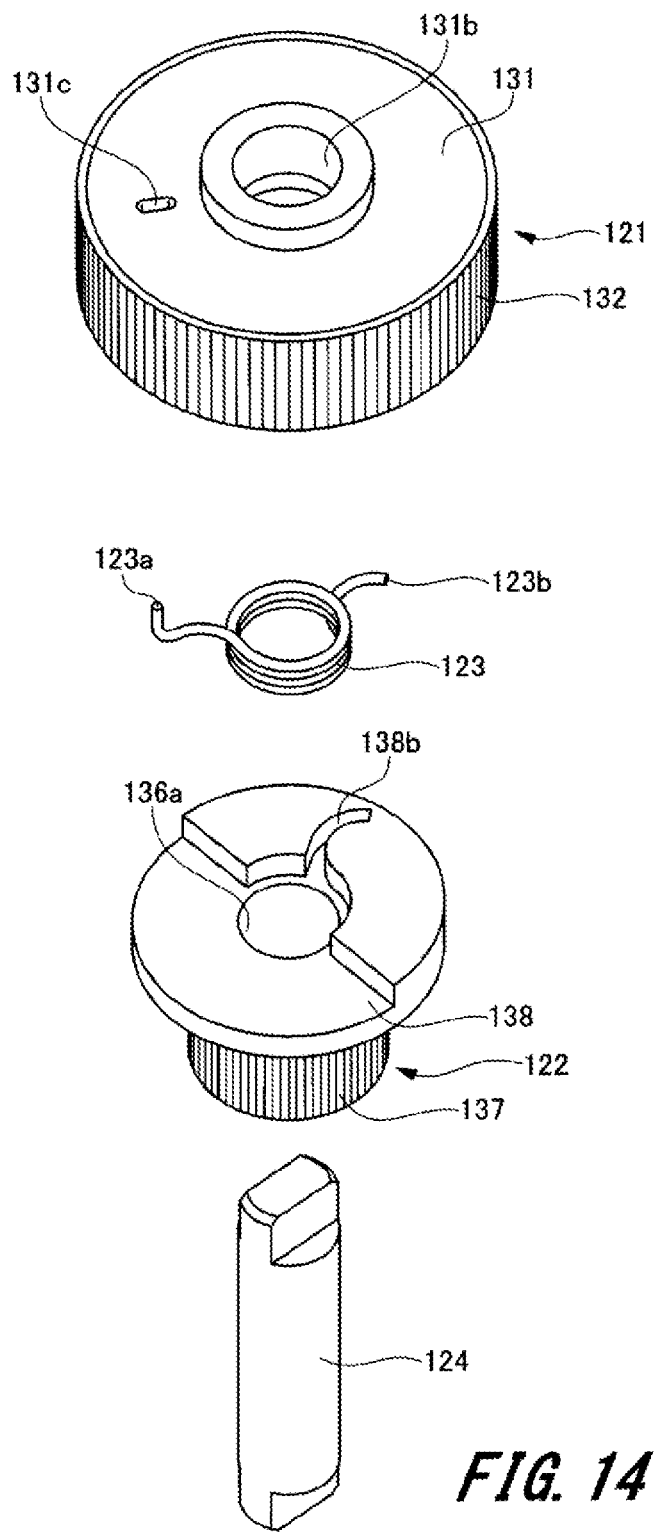
FIG. 14 is an exploded perspective view illustrating the occlusion detection mechanism of the liquid medicine administration apparatus according to the second exemplary embodiment.
Figure 15:
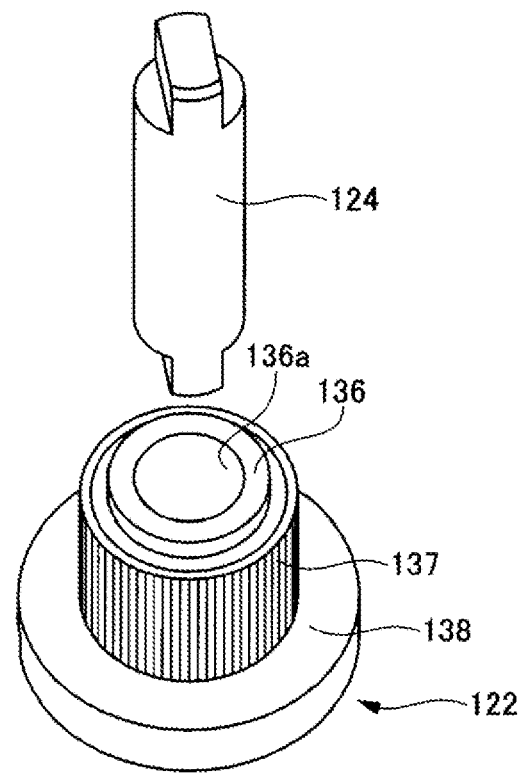
FIG. 15 is an exploded perspective view illustrating the occlusion detection mechanism of the liquid medicine administration apparatus according to the second exemplary embodiment.
Figure 15:
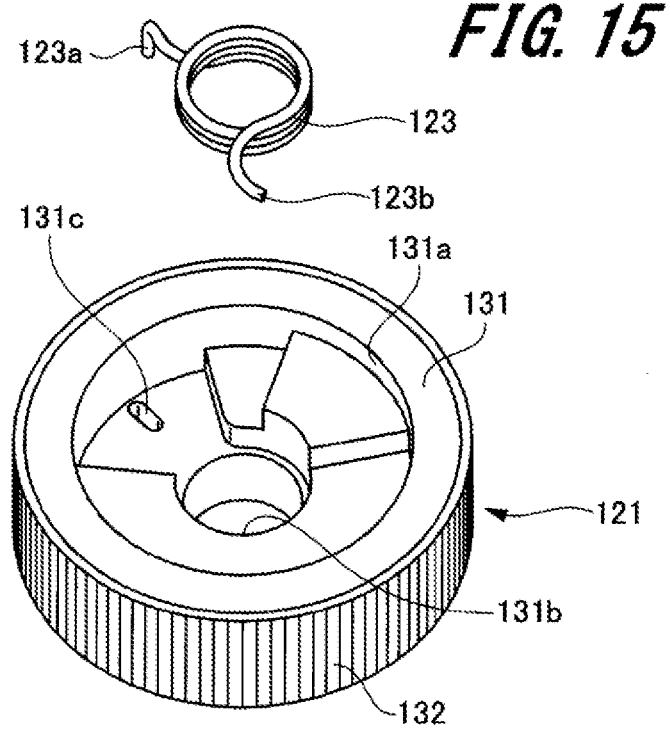
Figure 16:
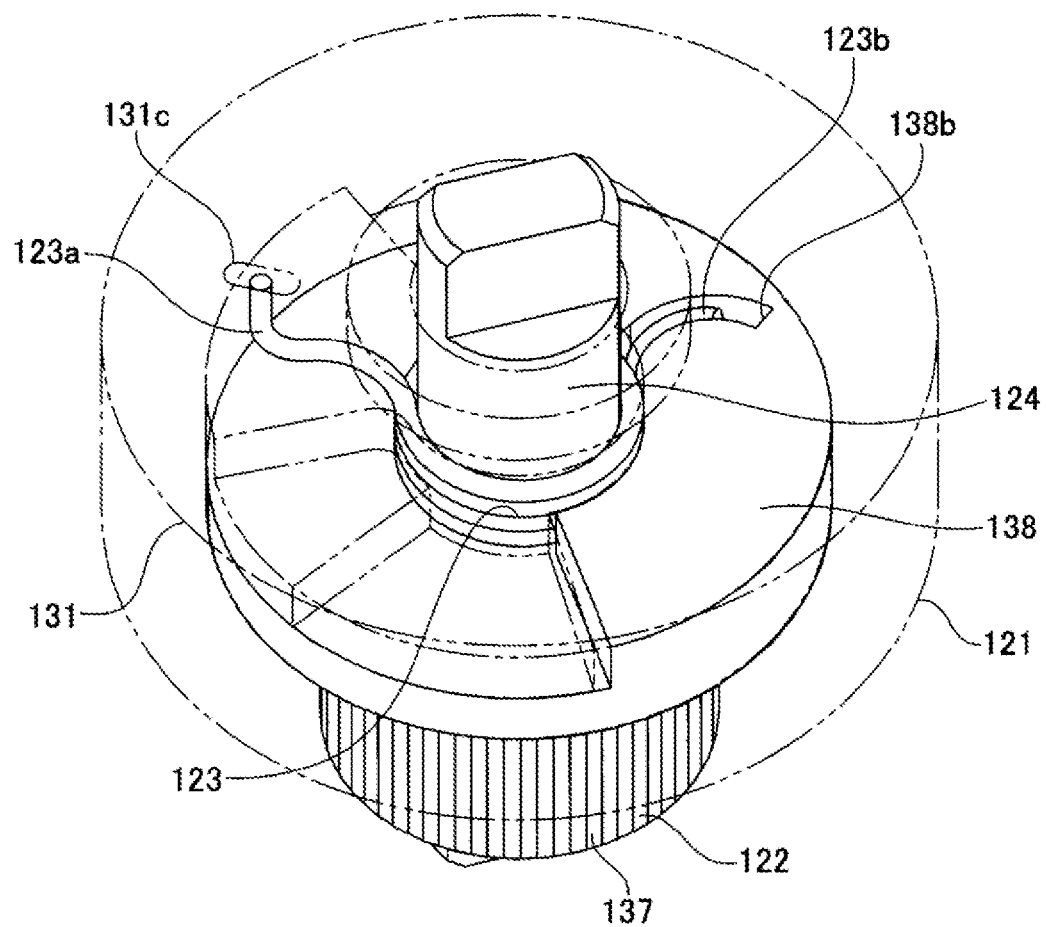
FIG. 16 is a see-through view of a portion of the occlusion detection mechanism of the liquid medicine administration apparatus according to the second exemplary embodiment.

FIG. 13 is a perspective view illustrating the occlusion detection mechanism 112, FIGS. 14 and 15 are exploded perspective views illustrating the occlusion detection mechanism 112, and FIG. 16 is a perspective view including a see-through view of a portion of the occlusion detection mechanism 112.

As illustrated in FIGS. 13 to 16, the occlusion detection mechanism 112 includes a drive side gear section 121, a pusher side gear section 122, a biasing member 123, and a fixing shaft 124. The drive side gear section 121 includes a columnar main body 131, and a drive side gear 132.

As illustrated in FIG. 15, an accommodation recess 131a is formed on one surface on the one axial end side of the main body 131. The accommodation recess 131a is a recess having one axial surface of the main body 131 that is recessed in a plurality of stages toward the other axial end. The main body 131 includes a through hole 131b and a fixing portion 131c.

The through hole 131b penetrates the main body 131 from one axial end to the other axial end. The fixing shaft 124 penetrates through the through hole 131b. The main body 131 is rotatably supported by the fixing shaft 124. The fixing portion 131c is provided at the bottom of the accommodation recess 131a. One end portion 123a of the biasing member 123 is fixed to the fixing portion 131c.

The drive side gear 132 is formed on a side peripheral portion of the main body 131. The drive side gear 132 meshes with the first gear 111 (refer to FIG. 12).

The pusher side gear section 122 includes a columnar main body 136, a pusher side gear 137, and a flange member 138. The pusher side gear 137 is formed on the side peripheral portion of the main body 136. The pusher side gear 137 meshes with the third gear section 113.

The flange member 138 is formed at one axial end portion of the main body 136. The flange member 138 protrudes radially outward at one end portion of the main body 136. The flange member 138 has a disk shape. A through hole 136a is formed in the axial center of the main body 136. The through hole 136a penetrates from the main body 136 to the flange member 138 in the axial direction. The fixing shaft 124 penetrates through the through hole 136a. The main body 136 and the flange member 138 are rotatably supported by the fixing shaft 124.

One surface of the flange member 138 opposite to the main body 136 includes a spring stopper portion 138b. The flange member 138 is inserted into the accommodation recess 131a formed in the main body 131 of the drive side gear section 121.

The biasing member 123 is constituted with a torsion coil spring, for example. The one end portion 123a of the biasing member 123 is fixed to the fixing portion 131c formed in the main body 131 of the drive side gear section 121. The other end portion 123b of the biasing member 123 is fixed to the spring stopper portion 138b of the pusher side gear section 122.

As illustrated in FIG. 16, the biasing member 123 is accommodated in the accommodation recess 131a of the drive side gear section 121 and is disposed between the main body 131 of the drive side gear section 121 and the flange member 138 of the pusher side gear section 122. The biasing member 123 is disposed around the fixing shaft 124 between the drive side gear section 121 and the pusher side gear section 122.

The fixing shaft 124 is fixed to a support portion (not illustrated) provided in the casing 11.

Next, occlusion detection operation of the occlusion detection mechanism 112 according to the above-configured second exemplary embodiment will be described with reference to FIG. 17.

Figure 17:
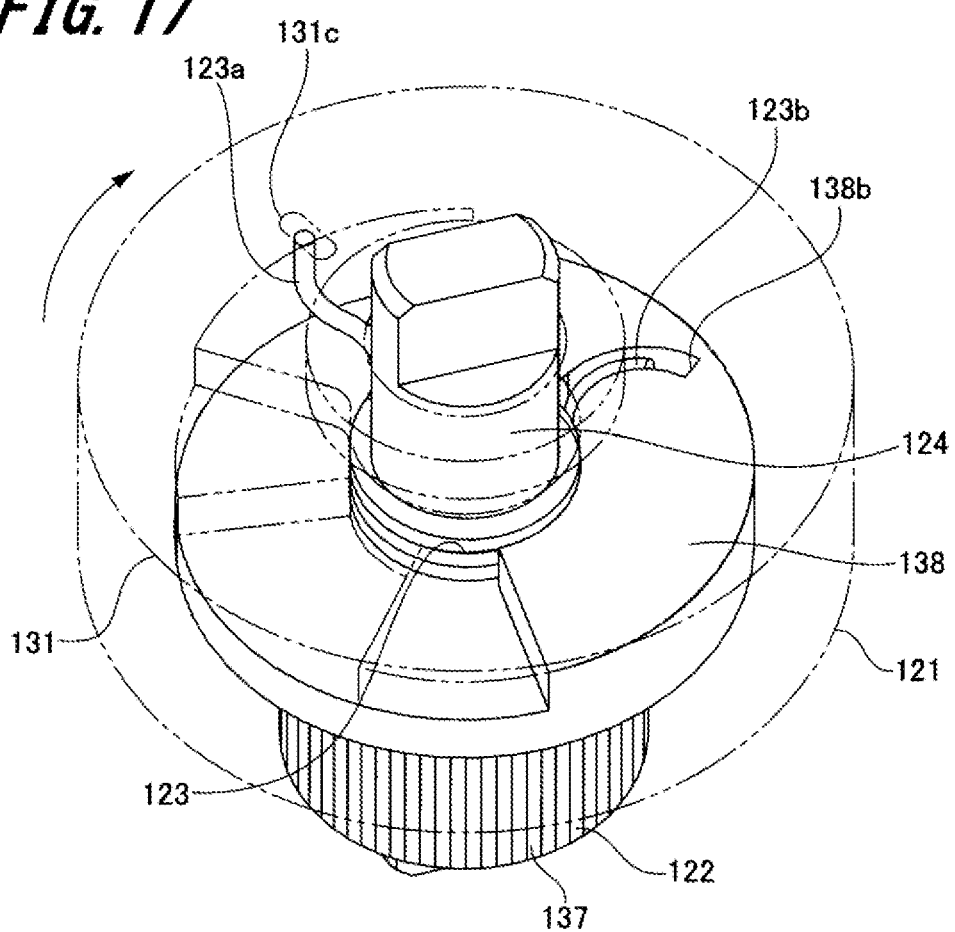
FIG. 17 is an explanatory view illustrating occlusion detection operation of the occlusion detection mechanism of the liquid medicine administration apparatus according to the second exemplary embodiment.

FIG. 17 is an explanatory view illustrating occlusion detection operation of the occlusion detection mechanism 112.

First, in a state in which the liquid medicine passage such as the cannula 6a is not occluded, the drive side gear section 121 rotates together with the pusher side gear section 122 in a state of being biased by the biasing member 123. In contrast, in a case where the liquid medicine passage pushed out by the pusher member 18 is occluded due to a certain factor, the rotational resistance (torque) applied to the operation gear 22a via the feed screw shaft 22b increases. This increase the torque applied to the pusher side gear 137 via the operation gear 22a, the fourth gear section 114, and the third gear section 113.

Here, the driving force is transmitted from the drive section 15 to the drive side gear section 121. Therefore, as illustrated in FIG. 17, a phase difference occurs between the rotation of the drive side gear section 121 and the rotation of the pusher side gear section 122. The drive side gear section 121 rotates faster than the pusher side gear section 122 against the biasing force of the biasing member 123. When the phase difference of rotation between the drive side gear section 121 and the pusher side gear section 122 increases, the biasing member 123 tightens the fixing shaft 124.

The biasing member 123 tightens the fixing shaft 124 to lock the rotation of the drive side gear section 121. That is, in the occlusion detection mechanism 112 according to the second exemplary embodiment, the biasing member 123 configures a locking mechanism.

When the rotation of the drive side gear section 121 is locked, the rotation of the first gear 111 meshing with the drive side gear 132 of the drive side gear section 121 is locked, and the rotation of the drive shaft 15a of the drive section 15 is also locked.

Because other configurations are similar to the configuration of the liquid medicine administration unit 1 according to the first exemplary embodiment, description will be omitted. The above-configured liquid medicine administration unit 101 can also obtain the similar operational effects as the liquid medicine administration unit 1 according to the first exemplary embodiment described above.

Moreover, according to the occlusion detection mechanism 112 of the second exemplary embodiment, the biasing force of the biasing member 123 can be adjusted to change the accuracy of occlusion detection according to the purpose.

Embodiments have been described as above, including their operational effects. The liquid medicine administration apparatus and the liquid medicine administration unit according to the present invention are not limited to the above-described embodiments, and various modifications are possible within the scope of the invention described in the claims.

While the above-described exemplary embodiment includes an example in which an elastic biasing member is used as the temporary retainer, the present invention is not limited to this example. The temporary retainer may be, for example, an engaging portion which temporarily retains the drive side gear section at a predetermined position with respect to the rotation shaft and disengages when a load equal to or larger than predetermined force is applied. Still, applying an elastic biasing member as the temporary retainer would overcome occlusion of the liquid medicine passage and would be able to automatically return to the initial state before the driving force of the drive section 15 stops.

REFERENCE NUMERAL LIST 1, 101 . . . Liquid medicine administration unit,
2, 102 . . . Liquid medicine administration apparatus,
3 . . . Cradle apparatus,
5 . . . Attachment section,
6 . . . Connection port,
6a . . . Cannula,
11 . . . Casing,
11a . . . First housing,
11b . . . Second housing,
12 . . . Lid member,
13 . . . Liquid medicine storage,
13a . . . Liquid delivery port,
13b . . . Filling port,
14, 104 . . . Transmission mechanism,
15 . . . Drive section,
15a . . . Drive shaft,
16 . . . Notification section,
17 . . . Battery housing,
18 . . . Pusher member,
18a . . . Gasket.
18b . . . Shaft member,
18c . . . Coupling portion,
19 . . . Liquid delivery pipe,
20 . . . Gear case,
20c . . . Protrusion (locking mechanism),
21 . . . Rotation detector,
21a . . . Detection sensor,
21b . . . Slit disk,
22 . . . Operation section,
22a . . . Operation gear,
22b . . . Feed screw shaft,
22c . . . Coupling nut,
31 . . . First gear,
32 . . . Second gear section,
33 . . . Third gear section,
34, 112 . . . Occlusion detection mechanism,
41, 121 . . . Drive side gear section,
42, 122 . . . Pusher side gear section,
43, 123 . . . Biasing member (temporary retainer),
44 . . . Rotation shaft,
44a . . . Shaft section,
44b . . . Spring receiving piece,
44c . . . Cam pin,
51 . . . Main body,
51a . . . Through hole,
51b . . . Cam groove,
52 . . . Drive side gear,
53 . . . Fixing protrusion (locking mechanism),
57 . . . Pusher side gear,
111 . . . First gear,
113 . . . Third gear section,
114 . . . Fourth gear section,
123a . . . End portion,
123b . . . End portion,
124 . . . Fixing shaft,.
131 . . . Columnar main body,
131a . . . Accommodation recess,
131b . . . Through hole,
131c . . . Fixing portion,
132 . . . Drive side gear,
136 . . . Columnar main body,
136a . . . Through hole, 137 . . . Pusher side gear,
138 . . . Flange member,
138b . . . Spring stopper portion

What is claimed is:

1. A liquid medicine administration apparatus comprising:
a drive section;
an operation section configured to operate a pusher member that is slidably located in a liquid medicine container;
a transmission mechanism configured to transmit a driving force of the drive section to the operation section;
an occlusion detection mechanism located in the transmission mechanism and configured to detect occlusion of a passage of liquid medicine administered from the liquid medicine container;
a rotation detector configured to detect rotation of the drive section; and
a notification section configured to notify a user when the rotation detector detects stoppage of the rotation of the drive section;
wherein the occlusion detection mechanism comprises:
a drive side gear section configured to mesh with a gear on a drive section side,
a pusher side gear section configured to rotate together with the drive side gear section and to mesh with a gear on an operation section side,
a locking mechanism configured to stop rotation of the drive side gear section when a rotational resistance applied to the pusher side gear section exceeds a predetermined amount,
a rotation shaft configured to rotatably support the drive side gear section and the pusher side gear section, and
a temporary retainer configured to temporarily retain the drive side gear section at a predetermined position with respect to the rotation shaft and
wherein the temporary retainer comprises an elastic member.

2. The liquid medicine administration apparatus according to claim 1, wherein:
the temporary retainer is configured to bias the drive side gear section toward the pusher side gear section; and
the locking mechanism comprises:
a protrusion located on one of (i) a casing accommodating the occlusion detection mechanism, or (ii) a gear case accommodating the drive side gear section, and
a fixing protrusion located on the drive side gear section and configured to abut the protrusion when the drive side gear section moves in a direction away from the pusher side gear section against biasing force of the temporary retainer.

3. The liquid medicine administration apparatus according to claim 1, wherein:
the locking mechanism is formed with the temporary retainer and is configured to tighten the rotation shaft to lock the rotation of the drive side gear section when the rotational resistance applied to the pusher side gear section exceeds the predetermined amount.

4. A liquid medicine administration unit comprising:
a liquid medicine administration apparatus including a liquid medicine container;
a cradle apparatus to which the liquid medicine administration apparatus is detachably attached; and
a connection port configured to be attached to the cradle apparatus and comprising a cannula configured to be punctured in a living body and to which a liquid medicine is supplied from the liquid medicine administration apparatus,
wherein the liquid medicine administration apparatus comprises:
a drive section;
an operation section configured to operate a pusher member that is slidably located in the liquid medicine container;
a transmission mechanism configured to transmit a driving force of the drive section to the operation section;
an occlusion detection mechanism located in the transmission mechanism and configured to detect occlusion of a passage of liquid medicine administered from the liquid medicine container;
a rotation detector configured to detect rotation of the drive section; and
a notification section configured to notify a user when the rotation detector detects stoppage of the rotation of the drive section;
wherein the occlusion detection mechanism comprises:
a drive side gear section configured to mesh with a gear on a drive section side,
a pusher side gear section configured to rotate together with the drive side gear section and to mesh with a gear on an operation section,
a locking mechanism configured to stop rotation of the drive side, gear section when a rotational resistance applied to the pusher side gear section exceeds a predetermined amount,
a rotation shaft configured to rotatably support the drive side gear section and the pusher side gear section, and
a temporary retainer configured to temporarily retain the drive side gear section at a predetermined position with respect to the rotation shaft; and
wherein the temporary retainer comprises an elastic member.

5. An occlusion detection method for a liquid medicine administration apparatus, the method comprising:
providing a liquid medicine administration apparatus comprising:
a drive section,
an operation section configured to operate a pusher member that is slidably located in a liquid medicine container,
a transmission mechanism configured to transmit driving force of the drive section to the operation section,
a drive side gear section configured to mesh with a gear on a drive section side,
a pusher side gear section configured to rotate together with the drive side gear section and to mesh with a gear on an operation section side, and
an occlusion detection mechanism comprising:
a rotation shaft configured to rotatably support the drive side gear section and the pusher side gear section, and
a temporary retainer configured to temporarily retain the drive side gear section at a predetermined position with respect to the rotation shaft;
stopping rotation of the drive side gear section when rotational resistance applied to the pusher side gear section exceeds a predetermined amount, and
detecting stoppage of rotation of the drive section to detect occlusion of a passage of liquid medicine administered from the liquid medicine container; and wherein the temporary retainer comprises an elastic member.

6. An occlusion detection method for a liquid medicine administration system, the method comprising:
providing a liquid medicine administration system comprising
a liquid medicine administration apparatus including a liquid medicine container,
a cradle apparatus to which the liquid medicine administration apparatus is detachably attached, and
a connection port configured to be attached to the cradle apparatus and comprising a cannula configured to be punctured in a living body and to which liquid medicine is supplied from the liquid medicine administration apparatus,
wherein the liquid medicine administration apparatus comprises:
a drive section,
an operation section configured to operate a pusher member slidably located in the liquid medicine container,
a transmission mechanism configured to transmit driving force of the drive section to the operation section,
a drive side gear section configured to mesh with a gear on a drive section side,
a pusher side gear section configured to rotate together with the drive side gear section and to mesh with a gear on an operation section side, and
an occlusion detection mechanism comprising:
a rotation shaft configured to rotatably support the drive side gear section and the pusher side gear section, and
a temporary retainer configured to temporarily retain the drive side gear section at a predetermined position with respect to the rotation shaft;
stopping rotation of the drive side gear section when rotational resistance applied to the pusher side gear section exceeds a predetermined amount; and
detecting stoppage of rotation of the drive section to detect occlusion of a passage of liquid medicine administered from the liquid medicine container; and
wherein the temporary retainer comprises an elastic member.

* * * * *